United States Patent [19]

Boucher, Jr.

[11] Patent Number: 5,628,984
[45] Date of Patent: May 13, 1997

[54] METHOD OF DETECTING LUNG DISEASE

[75] Inventor: Richard C. Boucher, Jr., Chapel Hill, N.C.

[73] Assignee: University of North Carolina at Chapel Hill, Chapel Hill, N.C.

[21] Appl. No.: 509,052

[22] Filed: Jul. 31, 1995

[51] Int. Cl.$^6$ ............... A61K 31/495; C08K 5/3462
[52] U.S. Cl. ..................... 424/45; 424/489; 424/9.1
[58] Field of Search ................................. 424/45

[56] References Cited

U.S. PATENT DOCUMENTS

| | | | |
|---|---|---|---|
| 4,501,729 | 2/1985 | Boucher et al. | 424/45 |
| 5,292,498 | 3/1994 | Boucher, Jr. | 424/45 |
| 5,420,116 | 5/1995 | Puchelle | 514/47 |

OTHER PUBLICATIONS

M.I. Lethem et al.; *Nucleotide Regulation of Goblet Cells in Human Airway Epithelial Explants: Normal Exocytosis in Cystic Fibrosis*, Am. J. Respir. Cell Mol. Biol. 9, 315–322 (1993).

K.N. Olivier, *Acute Safety and Effects on Mucociliary Clearance of Aerosolized Clearance of Aerosolized Uridine 5'–Triphosphate ± Amiloride in Normal Human Adults*, Am. J. Respir. Crit. Care Med. 154, 217–223 (1996).

Primary Examiner—Peter F. Kulkosky
Attorney, Agent, or Firm—Bell, Seltzer, Park & Gibson

[57] ABSTRACT

A method of faciltating the obtaining of a mucus sample from at least one lung of a subject comprises administering a physiologically acceptable salt to at least one lung of the subject in an amount effective to hydrate lung mucus secretions therein, and concurrently administering to said at least one lung of the subject, in an amount effective to hydrate lung mucous secretions therein, uridine triphosphate, an active analog thereof, or a pharmaceutically acceptable salt of either thereof. Pharmaceutical compositions useful for carrying out the method comprise, in combination, a physiologically acceptable salt, and uridine triphosphate, an active analog thereof, or a pharmaceutically acceptable salt of either thereof. The composition may be a liquid composition or a dry powder composition.

14 Claims, No Drawings

METHOD OF DETECTING LUNG DISEASE

This invention was made with Government support under grant number HL-SPO1-34322 from the National Institutes of Health (NIH). The Government has certain rights to this invention.

FIELD OF THE INVENTION

This application concerns lung diagnostic assays in general, and particularly concerns a lung diagnostic assay in which lung mucus secretions are hydrated to facilitate collection thereof.

BACKGROUND OF THE INVENTION

The analysis of sputum samples is particularly important in the treatment and diagnosis of many lung disorders, including lung cancer and tuberculosis (TB).

In particular, microbial infections of the lung are a serious problem in patients afflicted with acquired immune deficiency syndrome (AIDS). Two particularly problematic infections are *Pneumocystis carinii* pneumonia infections and mycobacterial infections.

*Pneumocystis carinii* pneumonia infections are typically referred to as "PCP" infections. It is now estimated that approximately 70 percent of patients afflicted with AIDS will contract this disease. PCP may be treated with pentamidine isethionate, but an unfortunate side effect of this treatment is its toxicity. Accordingly, there is a continued need for techniques which permit the rapid and convenient screening of AIDS patients for this disease, and for the rapid, early, and accurate diagnosis thereof.

Mycobacteria are a large, diverse, and widely distributed family of aerobic, nonsporulating, nonmotile bacilli that have a high cell-wall lipid content and a slow growth rate. Some Mycobacteria are harmless, while others are significant pathogens. The pathogenic Mycobacterium include *M. tuberculosis*, responsible for tuberculosis, as well as non-tuberculosis Mycobacteria such as *M. avium*, responsible for *Mycobacterium Avium* complex infections.

SUMMARY OF THE INVENTION

A first aspect of the present invention is a method of faciltating the obtaining of a mucus sample from at least one lung of a subject. The method comprises administering a physiologically acceptable salt to at least one lung of the subject in an amount effective to hydrate lung mucus secretions therein, and concurrently administering to said at least one lung of the subject, in an amount effective to hydrate lung mucous secretions therein, a compound of Formula (I) below, or a pharmaceutically acceptable salt thereof:

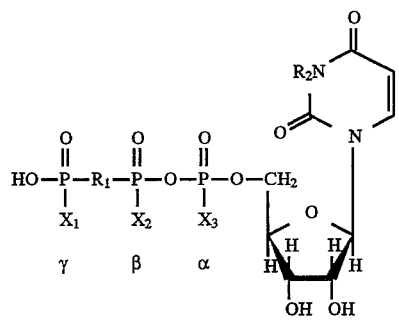

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br.

The method is accompanied or followed by the step of collecting a mucus sample from said at least one lung of said subject (e.g., by said subject expectorating a sputum sample).

A second aspect of the present invention is pharmaceutical composition useful for facilitating the collecting of a mucus sample from at least one lung of a subject, said composition comprising, in combination, a physiologically acceptable salt in an amount effective to hydrate lung mucus secretions; and a compound of Formula (I) as given above, or a pharmaceutically acceptable salt thereof, in an amount effective to hydrate lung mucus secretions. The composition may be a liquid composition or a dry powder composition.

DETAILED DESCRIPTION OF THE INVENTION

Compounds illustrative of the compounds of Formula (I) above (also referred to as "active compounds" herein) include: (a) uridine 5'-triphosphate (UTP); (b) uridine 5'-O-(3-thiotriphosphate) (UTPγS); and (c) 5-bromo-uridine 5'-triphosphate (5-BrUTP). One preferred compound of Formula (I) above is the UTP analog uridine 5'-O-(3-thiotriphosphate) (or "UTPγS"). These compounds are known or may be made in accordance with known procedures, or variations thereof which will be apparent to those skilled in the art. See generally U.S. Pat. No. 5,292,498 to Boucher; N. Cusack and S. Hourani, *Annals N.Y. Acad. Sci.* 603, 172–181 (G. Dubyak and J. Fedan Eds. 1990). For example, UTP may be made in the manner described in Kenner et al., *J. Chem. Soc.* 1954, 2288; or Hall and Khorana, *J. Chem. Soc.* 76, 5056 (1954). See Merck Index, Monograph No. 9795 (11th Ed. 1989). UTPγS may be made in the manner described in G. Goody and F. Eckstein, *J. Am. Chem. Soc.* 93, 6252 (1971).

For simplicity, Formula I herein illustrates uridine triphosphate active compounds in the naturally occurring D configuration, but the present invention also encompasses compounds in the L configuration, and mixtures of compounds in the D and L configurations, unless specified otherwise. The naturally occurring D configuration is preferred.

The active compounds disclosed herein can be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Amiloride (also known as 3,5,-diamino-6-chloro-N-(diaminomethylene)pyrazinecarboxamide), benzamil (also known as 3,5-diamino-6-chloro-N-(benzylaminoaminomethylene) pyrazinecarboxamide) and phenamil (also known as 3,5-diamino-6-chloro-N-(phenylaminoaminomethylene) pyrazinecarboxamide) are known compounds and are disclosed in U.S. Pat. No. 3,313,813 to E. Cragoe. The terms "amiloride," "benzamil," and "phenamil," as used herein (also refered to as "active compounds" herein), include the pharmaceutically acceptable salts thereof, such as (but not limited to) amiloridehydrochloride, benzamilhydrochloride or phenamil hydrochloride. Amiloride, benzamil or phenamil used to prepare compositions for the present invention may alternatively be in the form of a pharmaceutically acceptable free base of amiloride, benzamil or phenamil. Because the free base of the compound is less soluble than the salt, free base compositions are employed to provide more sustained release of benzamil or phenamil to the lungs.

Physiologically acceptable salts (also sometimes referred to as "active compounds" herein) used to carry out the method of the present invention are those that hydrate lung mucus secretions by facilitating the transport of water from lung endothelial cells into the mucus. Physiologcally acceptable salts are salts that retain the desired biological activity of hydrating lung mucus secretions and do not impart undesired toxicological effects. Examples of such salts include, but are not limited to, sodium chloride, potassium chloride, choline chloride, and N-methyl-D-glucamine chloride. Sodium chloride is currently preferred. These salts may be provided in the form of a dry respirable powder (discussed below) or as an aqueous saline solution.

The present invention is concerned primarily with the treatment of human subjects, but may also be employed for the treatment of other mammalian subjects, such as dogs and cats, for veterinary purposes.

The active compounds disclosed herein may be administered to the lung(s) of a subject by any suitable means. As used herein, the word "concurrently" means sufficiently close in time to produce a combined effect (that is, concurrently may be simultaneously, or it may be two or more events occuring within a short time period before or after each other). By "at least one lung" is meant that administration of active compounds may be to one or both lungs of the subject, but where administration is to only one lung, then administration of the various active compounds is to the same lung.

Active compounds are preferably administered by administering an aerosol suspension of respirable particles comprised of the active compound, which the subject inhales. The respirable particles may be liquid or solid. The particles may optionally contain other therapeutic ingredients such as amiloride, benzamil or phenamil, with the selected compound included in an amount effective to inhibit the reabsorption of water from airway mucous secretions, as described in U.S. Pat. No. 4,501,729 (applicant specifically intends the disclosure of this and all other patent references cited herein be incorporated herein by reference).

The particulate pharmaceutical composition may optionally contain a dispersant which serves to facilitate the formation of an aerosol. A suitable dispersant is lactose, which may be blended with the active compound or compounds in any suitable ratio (e.g., a 1 to 1 ratio by weight).

Particles comprised of active compound for practicing the present invention should include particles of respirable size: that is, particles of a size sufficiently small to pass through the mouth and larynx upon inhalation and into the bronchi and alveoli of the lungs. In general, particles ranging from about 1 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized. For nasal administration, a particle size in the range of 10–500 µm is preferred to ensure retention in the nasal cavity.

Liquid pharmaceutical compositions of active compound for producing an aerosol may be prepared by combining the active compound with a suitable vehicle, such as sterile pyrogen free water. The hypertonic saline solutions used to carry out the present invention are preferably sterile, pyrogen-free solutions, comprising from one to ten percent (by weight) of the physiologically acceptable salt, and more preferably from three to seven percent by weight of the physiologically acceptable salt. Where compounds of Formula (I) or the pharmaceutically acceptable salts thereof are included in the hypertonic saline solution, they are typically included in a concentration ranging from about $10^{-4}M$ to about $10^{-1}M$, and more preferably in a concentration ranging from about $10^{-2}M$ to about $10^{-1}M$. Other therapeutic compounds such as amiloride, benzamil or phenamil may optionally be included (when such compounds are included, the saline solution is preferably not more than 0.3 percent by weight of the physiologically acceptable salt, and more preferably is 0.12 percent by weight of the physiologically acceptable salt).

Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio (e.g., a 1 to 1 ratio by weight). Again, other therapeutic compounds such as amiloride, benzamil or phenamil may also be included.

Aerosols of liquid particles comprising the active compound may be produced by any suitable means, such as with a pressure-driven aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution, preferably made isotonic with body fluids by the addition of, for example, sodium chloride. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly. Typically, each aerosol is delivered to the patient for a period from about five to about 20 minutes, with a delivery period of about ten minutes being preferred.

The dosage of the compound of Formula (I), or the pharmaceutically acceptable salt thereof, will vary depending on the condition being treated and the state of the subject, but generally may be an amount sufficient to achieve dissolved concentrations of active compound on the airway surfaces of the subject of from about $10^{-9}$ to about $10^{-2}$ Moles/liter, more preferably from about $10^{-7}$ to about $10^{-3}$ Moles/liter, and most preferably from about $10^{-6}$ to about $10^{-4}$ Moles/liter. Depending upon the solubility of the particular formulation of active compound administered, the daily dose may be divided among one or several unit dose administrations.

When the sputum sample is subjected to cytological, bacterial or DNA analysis for detecting infectious microbial species therein, the sputum sample may first be digested with a liquefying agent, such as N-acetyl-L-cystein (NALC) and sodium hydroxide.

As noted above, the present invention is particularly useful for collecting mucus samples which are used for detecting Pneumocystis carinii pneumonia and Mycobacteria infections. The term "Mycobacteria" as used herein has its conventional meaning in the art referring to acid-fast, non-motile, rod shaped bacteria. See generally B. Davis et al., Microbiology, 724–742 (#d. Ed. 1980). All generally belong to the family Mycobacteriaceae. By way of example, the mycobacteria include, but are not limited to, *Mycobacterium africanum, M. avium, M. bovis, M. bovis*-BCG, *M. chelonae, M. fortuitum, M. gordonae, M. intracellulae, M. kansasii, M. leprae, M. microti, M. paratuberculosis, M. scrofulaceum,* and *M. tuberculosis*. The present invention is useful in diagnosing both tuberculosis and non-tuberculosis Mycobacteria, and is useful in diagnosing *M. avium* complex infections.

The present invention is explained in greater detail in the following non-limiting Examples.

EXAMPLE 1

Delivery of UTP followed by Hypertonic Saline

A subject is caused to inhale an aerosol of UTP solution ($10^{-2}$M UTP in 0.9% (by weight) sterile pyrogen-free saline solution) delivered by an Omron ultrasonic nebulizer for 10 minutes. Immediately afterwards, the subject is caused to inhale an aerosol of hypertonic saline solution (3% sterile pyrogen-free saline solution), delivered by a DeVilbis ultrasonic nebulizer for 10 minutes. During inhalation of the aerosols and after inhalation of the aerosols, the subject is encouraged to cough, and all sputum is collected during aerosol inhalation and over a 20 minute interval following cessation of aerosol inhalation. The sputum is captured in a plastic sputum container. The sputum so obtained is analyzed for content pending the clinical requirement, including analyses of cytologies for pulmonary neoplasm, and the presence of infectious agents such *Pneumocystis carinii* via silver staining and immunofluorescence techniques. The technique is applicable for the diagnoses of other microorganisms in the lower lung, including bacterial, viral, amd microplasma, using culture, immunocytochemical, and molecular (PCR, in situ hybridization) techniques.

EXAMPLE 2

Delivery of UTP with Amiloride

This example is carried out in essentially the same manner as example 1 above, except that the UTP is dissolved in a 0.12% sterile pyrogen-free NaCl solution, and the solution also contains $10^{-2}$M amiloride.

EXAMPLE 3

Delivery of Hypertonic Saline followed by UTP

This Example is carried out in essentially the same manner as Example 1 above, except that the hypertonic saline solution is delivered first, and the UTP solution is delivered immediately thereafter. Durations of delivery and concentrations remain the same.

EXAMPLE 4

Concurrent Delivery of UTP in Hypertonic Saline

This Example is carried out by modification of Example 1 above, with $10^{-1}$ UTP being diluted in the hypertonic saline solutiion so that a single solution is delivered to the patient by inhalation of an aerosol generated by the Omron ultrasonic nebulizer for a period of 15 minutes.

The foregoing examples are illustrative of the present invention, and are not to be construed as limiting thereof. Among other things, volumes, times, and amounts can be varied from those specifically set forth above. Accordingly, the invention is defined by the following claims, with equivalents of the claims to be included therein.

That which is claimed is:

1. A method of facilitating the obtaining of a mucus sample from at least one lung of a subject, comprising:
   administering by inhalation a physiologically acceptable salt to at least one lung of said subject in an amount effective to hydrate lung mucus secretions therein, wherein said physiologically acceptable salt facilitates the removal of said lung mucus from said lung, and concurrently administering by inhalation to said at least one lung of said subject, in an amount effective to stimulate the secretion of lung mucus therein, a compound of Formula (I) below, or a pharmaceutically acceptable salt thereof:

$$\text{(I)}$$

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br.

2. A method according to claim 1, wherein said physiologically acceptable salt is administered by administering an aqueous solution containing both said salt and said compound of Formula (I) or said pharmaceutically acceptable salt thereof.

3. A method according to claim 1, wherein said compound of Formula (I), or said pharmaceutically acceptable salt thereof, is administered in an amount sufficient to achieve concentrations thereof on the airway surfaces of said subject of from about $10^{-9}$ to about $10^{-3}$ Moles/liter.

4. A method according to claim 1, further comprising concurrently administering a compound selected from the group consisting of amiloride, benzamil and phenamil, and pharmaceutically acceptable salts thereof, to said subject in an amount effective to inhibit the reabsorption of water from lung mucous secretions.

5. A method according to claim 1, wherein $X_2$ and $X_3$ are OH.

6. A method according to claim 1, wherein $R_1$ is oxygen.

7. A method according to claim 1, wherein $R_2$ is H.

8. A method according to claim 1, wherein said compound is selected from the group consisting of uridine 5'-triphosphate, uridine 5'-O-(3-thiotriphosphate), and the pharmaceutically acceptable salts thereof.

9. A method according to claim 1, wherein said physiologically acceptable salt is selected from the group consisting of sodium chloride, potassium chloride, choline chloride, and N-methyl-D-glucamine chloride.

10. A method according to claim 1, wherein said physiologically acceptable salt is sodium chloride.

11. A method according to claim 1, wherein said physiologically acceptable salt and said compound of Formula (I) or said pharmaceutically acceptable salt thereof are delivered by administering an aerosol suspension of respirable particles comprised thereof to the said at least one lung of said subject.

12. A method according to claim 11, wherein said particles are selected from the group consisting of solid particles and liquid particles.

13. A method according to claim 11, wherein said aerosol is comprised of particles having a particle size within the range of about 1 to 10 microns.

14. A method according to claim 1, wherein said physiologically acceptable salt is sodium chloride.

* * * * *

UNITED STATES PATENT AND TRADEMARK OFFICE
CERTIFICATE OF CORRECTION

PATENT NO. : 5,628,984
DATED : May 13, 1997
INVENTOR(S) : Richard C. Boucher, Jr.

It is certified that error appears in the above-identified patent and that said Letters Patent is hereby corrected as shown below:

In the Summary of the Invention, at column 1, line 52, the chemical structure that appears as:

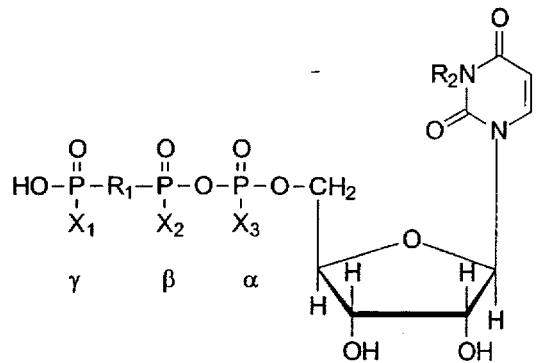

Should appear as:

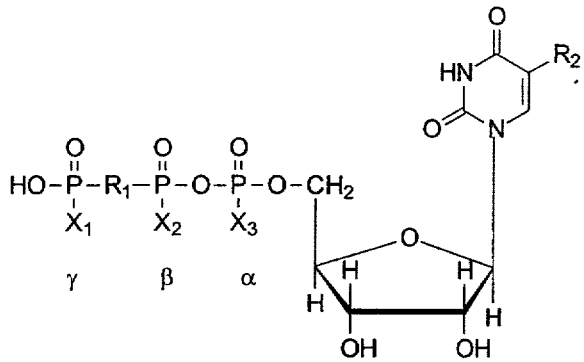

UNITED STATES PATENT AND TRADEMARK OFFICE
CERTIFICATE OF CORRECTION

PATENT NO. : 5,628,984
DATED : May 13, 1997
INVENTOR(S) : Richard C. Boucher, Jr.

It is certified that error appears in the above-identified patent and that said Letters Patent is hereby corrected as shown below:

In claim 1 at column 6, line 20, the chemical structure that appears as:

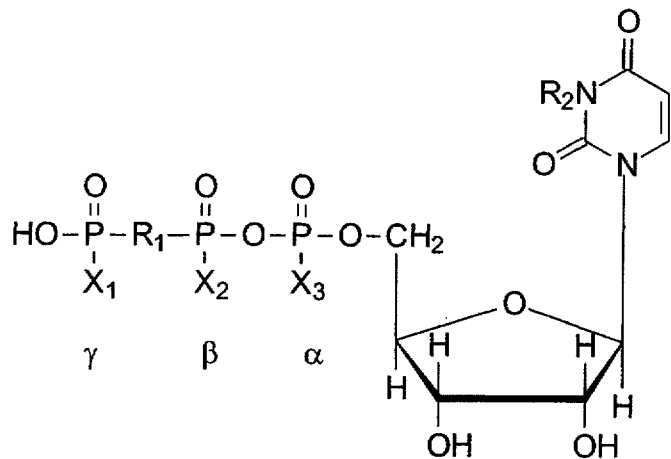

Should appear as:

UNITED STATES PATENT AND TRADEMARK OFFICE
CERTIFICATE OF CORRECTION

PATENT NO. : 5,628,984  
DATED : May 13, 1997  
INVENTOR(S) : Richard C. Boucher, Jr.

It is certified that error appears in the above-identified patent and that said Letters Patent is hereby corrected as shown below:

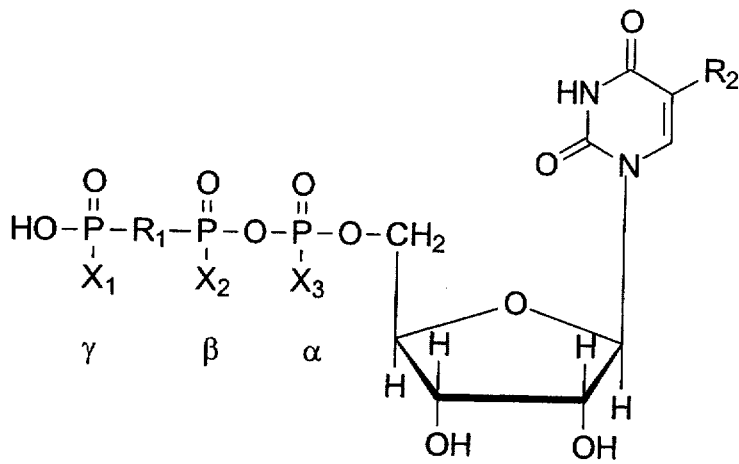

Signed and Sealed this

Second Day of February, 1999

Attest:

*Attesting Officer*

Acting Commissioner of Patents and Trademarks